US010913940B2

(12) United States Patent
Pourtaheri et al.

(10) Patent No.: US 10,913,940 B2
(45) Date of Patent: Feb. 9, 2021

(54) COMPOSITIONS AND METHODS FOR PESTICIDE DEGRADATION

(71) Applicant: UNIVERSITY OF VIRGINIA PATENT FOUNDATION, Charlottesville, VA (US)

(72) Inventors: Payam Pourtaheri, Sterling, VA (US); Sepehr Zomorodi, Herndon, VA (US); Zachery George Davis, Rice, VA (US); Ameer Hamza Shakeel, Ashburn, VA (US); Joseph Frank, Charlottesville, VA (US); Shaun Rafie Moshasha, Charlottesville, VA (US); Andrei Khokhlachev, Charlottesville, VA (US); Mark Kester, Afton, VA (US)

(73) Assignee: UNIVERSITY OF VIRGINIA, Charlottesville, VA (US)

( * ) Notice: Subject to any disclaimer, the term of this patent is extended or adjusted under 35 U.S.C. 154(b) by 0 days.

(21) Appl. No.: 16/092,697

(22) PCT Filed: Apr. 11, 2017

(86) PCT No.: PCT/US2017/027048

§ 371 (c)(1),
(2) Date: Oct. 10, 2018

(87) PCT Pub. No.: WO2017/180650

PCT Pub. Date: Oct. 19, 2017

(65) Prior Publication Data

US 2019/0169582 A1 Jun. 6, 2019

Related U.S. Application Data

(60) Provisional application No. 62/320,790, filed on Apr. 11, 2016.

(51) Int. Cl.

| | |
|---|---|
| ***C12P 21/02*** | (2006.01) |
| ***C12N 9/16*** | (2006.01) |
| ***C07K 14/195*** | (2006.01) |
| ***A62D 3/02*** | (2007.01) |
| *A62D 101/04* | (2007.01) |
| *A62D 101/26* | (2007.01) |

(52) U.S. Cl.
CPC ................ *C12N 9/16* (2013.01); *A62D 3/02* (2013.01); *C07K 14/195* (2013.01); *C12Y 301/08002* (2013.01); *A62D 2101/04* (2013.01); *A62D 2101/26* (2013.01); *C07K 2319/00* (2013.01)

(58) Field of Classification Search
CPC ...... C12P 21/02; C07K 16/00; C12N 15/1037
See application file for complete search history.

(56) References Cited

U.S. PATENT DOCUMENTS

| | | | | |
|---|---|---|---|---|
| 2003/0166099 | A1* | 9/2003 | Sabbadini .......... | C12N 15/1037 506/10 |
| 2005/0176117 | A1 | 8/2005 | Russell et al. | |
| 2006/0039870 | A1 | 2/2006 | Turner | |
| 2012/0107875 | A1 | 5/2012 | Liu et al. | |
| 2015/0218254 | A1 | 8/2015 | Sabbadini et al. | |

FOREIGN PATENT DOCUMENTS

| | | |
|---|---|---|
| CN | 101935669 A | 1/2011 |

OTHER PUBLICATIONS

Aislabie et al. 1995; A review of bacterial degradation of pesticides. Aust. J. Soil. Res. 33: 925-942.*
Singh et al. 2006; Microbial degradation of organophosphorus compounds (FEMS Microbiol. Rev. 30: 428-471.*
International Search Report dated Jul. 10, 2017, issued in PCT application (No. PCT/US2017/027048).
Written Opinion dated Jul. 10, 2017, issued PCT application (No. PCT/US2017/027048).

* cited by examiner

*Primary Examiner* — Karen Cochrane Carlson
(74) *Attorney, Agent, or Firm* — Potomac Law Group, PLLC

(57) ABSTRACT

Compositions and methods related to anucelate cells (e.g., bacterial minicells) for pesticide degradation applications including related cells, polypeptides, and vectors.

20 Claims, 11 Drawing Sheets

Specification includes a Sequence Listing.

SYMMETRIC BACTERIAL CELL DIVISION BY OVEREXPRESSION OF FILAMENTING TEMPERATURE-SENSITIVE MUTANT Z (ftsZ) PROTEIN

CONSTRUCTION OF MINICELL-INDUCING PLASMIDS

FLUORESCENCE MICROSCOPY VISUALIZATION OF BACTERIAL CELLS AND BUDDING MINICELLS EXPRESSING GREEN FLUORESCENT PROTEIN (GFP) ON THEIR OUTER MEMBRANES

INDUCTION OF MINICELL-FORMATION AND MINICELLS POST-PURIFICATION

FLUORESCENCE STAINING DEMONSTRATING THAT MINICELLS LACK NUCLEOID DNA BUT RETAIN MEMBRANE PROTEINS

EXEMPLARY PLASMID CONSTRUCT FOR SURFACE EXPRESSION OF ORGANOPHOSPHATE HYDROLASE (OPH)

Minicell formation in *E. coli*

Scanning Electron Microscope images of minicells expressing OPH expressing on their surface

DEGRADATION OF PARAOXON (ORGANOPHOSPHATE) BY MINICELLS EXPRESSING ORGANOPHOSPHATE HYDROLASE (OPH) ON THEIR SURFACE

COMPOSITIONS AND METHODS FOR PESTICIDE DEGRADATION

CROSS-REFERENCE TO RELATED APPLICATIONS

This application is a 371 national phase of International Application No. PCT/US2017/027048 filed Apr. 11, 2017 and published as WO 2017/0180650, which claims priority to U.S. Provisional Patent Application Ser. No. 62/320,790 filed on 11 Apr. 2016, each of which is incorporated herein by reference in its entirety.

REFERENCE TO SEQUENCE LISTING SUBMITTED ELECTRONICALLY VIA EFS-WEB

The entire content of the following electronic submission of the sequence listing submitted via the USPTO EFS-WEB server is incorporated herein by reference in its entirety for all purposes. The sequence listing is within the electronically filed text file that is identified as follows:
File Name: UVA_SEQL_ST25.txt
Date of Creation: 8 Oct. 2018
Size (bytes): 1,055 bytes

TECHNICAL FIELD OF THE INVENTION

The invention relates generally to compositions and methods concerning pesticide degradation. In particular, the invention relates to compositions and methods concerning production of bacterial minicells for use in pesticide degradation. The aforementioned compositions and methods also concern related cells (e.g., minicell-producing host cells), polypeptides, and vectors.

BACKGROUND OF THE INVENTION

Pesticides (e.g., insecticides, herbicides, and fungicides) are widely used in agriculture to control weeds, insect infestation and diseases. While the widespread use of pesticides has had several benefits for the agricultural industry in terms of combating the adverse economic impact of pest-related crop loss, excessive pesticide use poses significant problems to the environment and health. For example, the appearance and quality of crops and fruits sprayed with massive amounts of pesticide are significantly compromised. Further, excessive pesticide exposure leads to detrimental health effects such as nausea, seizures, and even death.

In view of the adverse effects produced by exposure to these compounds, it is essential to reduce, eliminate, or detoxify pesticides from crops and the environment. Various bioremediation approaches have been developed, such as enzyme-mediated decontamination and genetically-engineered organisms for specific bioremediation applications. However, biosafety concerns hinder synthetic biology applications because microorganisms (e.g., bacteria) rapidly replicate and may contain one or more antibiotic resistance genes. Thus, there is a critical need to develop safe, convenient, and economically-feasible methods for pesticide detoxification or removal.

As discussed herein, aspects of the present invention address the aforementioned challenges and unmet needs by providing bacterially-derived minicells for pesticide degradation, which are devoid of chromosomal DNA, and therefore unable to replicate and cause infection or ecological harm.

The compositions and methods of the present invention provide a solution for optimizing and/or reducing pre-harvest intervals (PHI) for a crop or an agricultural product, such as grapes, peaches, apples, sweet bell peppers, celery, nectarines, strawberries, cherries, pears, spinach, lettuce, and potatoes. The pre-harvest interval (PHI) is established by the Environmental Protection Agency (EPA) and describes the minimum period of time that must elapse between the application of pesticides to for a crop or an agricultural product and their harvest. The pre-harvest interval is a function of a pesticide's use pattern and of the amount of pesticide residues allowed on the crop at harvest. PHIs may range from a week to more than two months depending upon the pesticide, and limits the frequency at which a crop or an agricultural product may be harvested. Accordingly, the compositions and methods of the present invention potentially provide farmers with much needed solution to achieve premium harvests and premium marketing opportunities by encouraging regulatory changes in view of the reduction in the half-life of pesticides.

BRIEF SUMMARY OF THE INVENTION

The present invention provides compositions comprising a plurality of intact, bacterially-derived minicells, wherein each minicell of said plurality comprises a biologically active polypeptide displayed on the surface of the bacterial minicell, wherein said biologically active polypeptide has pesticide degrading activity. In certain embodiments, the bacterially-derived minicells are produced from a strain of *Escherichia coli, Bacillus* spp., *Salmonella* spp., *Listeria* spp., *Mycobacterium* spp., *Shigella* spp., or *Yersinia* spp. In certain embodiments, the pesticide is selected from the group consisting of organophosphates, glyphosates, neonicotinoids, carbamates, organochlorines, pyrethroids, Stribilurins, anilenes, thiophthlamadies (Captan), aromatic hydrocarbons, nitriles, cyanoimidazoles, demethylation inhibitors, phenylpyrroles, carboximides, phosphonates, dicarboximides, phenylamides, polyoxins, benzimidazoles, aryloxyphenoxy propionates, cyclohexanediones, phenylpyrazolin, imidazolinones, sulfonylamino-carbonyltriazolinones, amides, sulfonylureas, pyraxoles, triazolpyramidines, triazolones, dinitroanilines, benzoic acids, carboxylic acids, piconolinic acids, phenoxys, phenyl-carbamates, triazines, triazinones, uracils, benzthiadiazoles, ureas, thiocarbamates, triazoles, aryl triazones, chloroacetamides, pyrazoles, benzofuranyl alkylsulfonates, semicarbazones, bipyridyliums, and benzopyrazoles. In certain embodiments, the pesticide is an organophosphate selected from the group consisting of paraoxon, malathion, parathion, diazinon, naled, fenthion, dichlorvos, chlorpyrifos, phosmet, acephate, ethion, soman, sarin, tabun, VX, echothiophate, isoflurophate, trichlorfon, tetrachlorvinphos, azamethiphos, and azinphos-methyl. In particular embodiments, the pesticide comprises malathion.

In some embodiments, the biologically active polypeptide comprises a fusion protein. In some embodiments, the fusion protein comprises at least one surface-expressing moiety and at least one enzyme moiety. In some embodiments, the surface-expressing moiety comprises an ice nucleation protein (INPNC) or an exported bacterial protein, including wild type or mutant versions thereof. Contemplated exported bacterial proteins include LamB (λ receptor), OprF, OmpA (3a, II), Lpp (lipoprotein), MalE (maltose-binding protein), PhoA (alkaline phosphatase), Bla (TEM-1

β-lactamse, f1 or M13 major coat, f1 or M13 minor coat, and any wild type or mutant versions thereof. Contemplated enzyme moieties hydrolases, lipases, phospholipases, transacylases, transaminases, pectinase, proteases, amylases, cellulases, cutinases, esterases, acylases, invertases, isomerases, lyases, glucosidases, oxidoreductases, transferases, ligases, amidases, manganese peroxidase, laccase, lignin peroxidase, horseradish peroxidase or phosphonate dehydrogenase, cytosolic aldehyde oxidase, carbaryl hydrolases, and amidases, HCH dehydrochlorinase, haloalkane dehalogenase, pyrethroid hydrolases (PytH, EspA) and permethrinase.

In particular embodiments, the enzyme moiety comprises an organophosphate hydrolase. In some embodiments, a hydrolase is a phosphotriesterase, methyl parathion hydrolase, or organophosphorus acid anhydrolases.

In some embodiments, a second polypeptide is displayed on the surface of the bacterial minicell to increase adhesion to plants. In some embodiments, the second polypeptide comprises a fusion protein. In some embodiments, the fusion protein comprises at least one surface-expressing moiety and at least one plant cell adhesion moiety. Contemplated surface-expressing moieties include exported bacterial proteins such as LamB (λ receptor), OprF, OmpA (3a, II), Lpp (lipoprotein), MalE (maltose-binding protein), PhoA (alkaline phosphatase), Bla (TEM-1 β-lactamse, f1 or M13 major coat, f1 or M13 minor coat and any wild type or mutant versions thereof. Contemplated plant cell adhesion moieties include fusion proteins comprising a cellulose binding domain.

In some embodiments, minicells are at least 90-95% purity (i.e., free of detectable contaminants). In some embodiments, minicells are about 0.4 μm to about 0.5 μm in diameter.

The present invention also provides methods for pesticide degradation, comprising contacting a crop or an agricultural product with a composition in accordance with the present invention, wherein the composition mediates degradation of the pesticide to yield inert by-products.

The present invention also provides methods for bioremediation, comprising contacting a crop or an agricultural product with a composition in accordance with the present invention, wherein the composition mediates degradation of the pesticide to yield inert by-products.

The present invention also provides methods for reducing the half-life of a pesticide, the method comprising contacting a crop or agricultural product with the composition in accordance with the present invention. In some embodiments, the pesticide comprises malathion. In some embodiments, the half-life of malathion is reduced to about 1 hour, to about 2 hours, to about 3 hours, or to about 4 hours.

The present invention provides compositions and methods that are useful in degrading pesticides applied to, or otherwise present on, a crop or agricultural product such as grapes, peaches, apples, sweet bell peppers, celery, nectarines, strawberries, cherries, pears, spinach, lettuce, or potatoes.

BRIEF SUMMARY OF THE SEVERAL VIEWS OF THE DRAWINGS

FIG. 2A depicts a synthesized K-12 *E. coli* filamenting temperature-sensitive mutant Z (ftsZ) gene cloned into pSB1C3 (BBa_K1011000). FIG. 2B depicts a minicell-inducing construct (BBa_K1011001) which includes IPTG-inducible promoter (BBa_R0011), ribosomal binding sequence (RBS, BBa_B0034), synthesized K-12 *E. coli* ftsZ gene (BBa_K1011000), RBS (BBa_B0034), GFP (BBa_E0040), and double terminator (BBa_B0015) in pSB1C3.

FIG. 5A depicts the appearance of green glowing minicells 90 minutes following induction of the bacterial cells. The tiny brighter green spots appear to be minicells. FIG. 5B depicts minicells separated using centrifugation, antibiotics, and a sequence of filters to achieve about 95% purity of a minicell sample.

FIGS. 7A and 7B show representations of the same construct. The construct expresses a truncated ice nucleation protein (INPC)-OPH fusion protein where the INPC serves as a surface anchor to display OPH on the minicell surface.

FIGS. 9A-9B show scanning electron microscope images of minicells expressing OPH expressing on their surface. The average size of a minicell is around 0.5 micrometers (FIG. 9A). Minicells increase in size after each separation because the parent bacterial cell elongates, making the next minicell a little bigger than the first (FIG. 9B). FIG. 9C shows a graphical representation of the size distribution by intensity. Two peaks were obtained during sizing. The smaller peak is believed to be due to minor levels of contamination (e.g., dust). The higher peak around 500 nanometers is the minicell peak.

FIG. 10A corresponds to paraoxon degradation observed after one hour after induction of the bacterial cells to produce minicells expressing OPH. FIG. 10B corresponds to paraoxon degradation observed 24 hours following induction of bacterial cells to produce surface OPH-expressing minicells. As shown in FIG. 10B, more efficient degradation is observed after 24 hours.

DETAILED DESCRIPTION OF THE INVENTION

Figure 1:
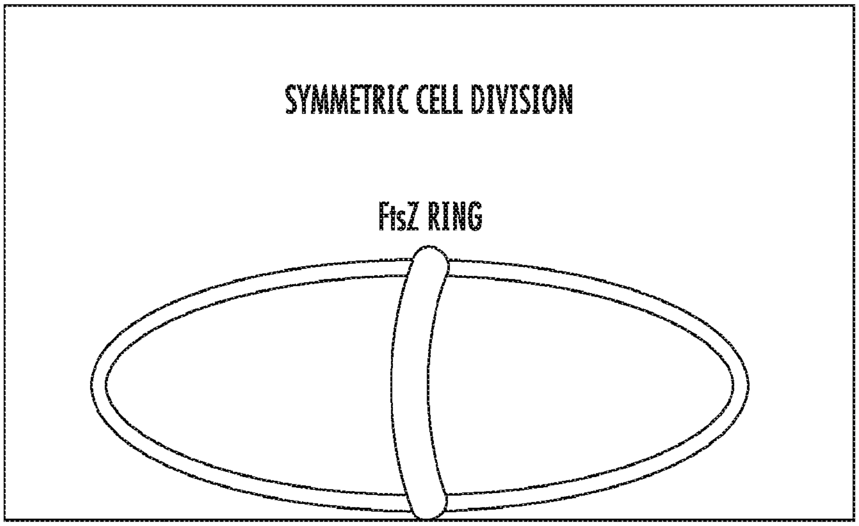
FIG. 1: Symmetric bacterial cell division by overexpression of ftsZ protein.

Unless defined otherwise, all technical and scientific terms used herein have the same meaning as commonly understood by one of ordinary skill in the art to which the disclosure is related. For example, the Concise Dictionary of Biomedicine and Molecular Biology, Juo, Pei-Show, 2$^{nd}$ ed. 2002, CRC Press; The Dictionary of Cell and Molecular Biology, 3$^{rd}$ ed., 1999, Academic Press; and the Oxford Dictionary of Biochemistry and Molecular Biology, Revised 2000, Oxford University Press, provide one of skill in the art with a general dictionary of many of the terms used herein. Additional definitions are set forth throughout the detailed description.

The present invention relates generally to compositions and methods concerning pesticide degradation. In particular, the invention relates to compositions and methods concerning production of minicells, including but not limited to eubacterial minicells for use in pesticide degradation. In certain aspects, the present invention provides minicells (e.g., bacterial minicells) comprising an organophosphate degrading enzyme (e.g., an organophosphorous hydrolase (OPH)) displayed on the minicell surface to biologically degrade organophosphates. In certain aspects, the present invention provides minicells comprising an organophosphate degrading enzyme (e.g., an organophosphorous hydrolase (OPH)) and/or a polypeptide having plant adhesion properties (e.g., a cellulose binding domain (CBD)) displayed on the minicell surface to selectively adhere to target plants and to biologically degrade organophosphates.

Minicells are the result of aberrant, asymmetric cell division, and contain membranes, peptidoglycan, ribosomes, RNA, protein, and often plasmids but no chromosome. (Frazer and Curtiss III, Production, Properties and Utility of Bacterial Minicells, 69, *Curr. Top. Microbiol. Immunol.* 1-3 (1975)). Because minicells lack chromosomal DNA, minicells cannot divide or grow, but they can continue other cellular processes, such as ATP synthesis, replication and transcription of plasmid DNA, and translation of mRNA. Although chromosomes do not segregate into minicells, extrachromosomal and/or episomal genetic expression elements will segregate, or may be introduced into minicells after segregation from parent cells.

In certain aspects, the invention provides a composition comprising a plurality of minicells, wherein each minicell of said plurality comprises a biologically active polypeptide displayed on the surface of the minicell, wherein said biologically active polypeptide has pesticide degrading activity. In certain aspects, the invention provides a composition comprising a plurality of intact, bacterially-derived minicells, wherein each minicell of said plurality comprises a biologically active polypeptide displayed on the surface of the bacterial minicell, wherein said biologically active polypeptide has pesticide degrading activity. In some embodiments, the composition comprises minicells which further comprise a second polypeptide displayed on the surface of the bacterial minicell, to increase adhesion to plants. In some embodiments, the composition comprises a mixture of minicells, wherein certain minicells within the mixed minicell population display the biologically active polypeptide or display the plant adhesion increasing polypeptide or display both. In certain embodiments, the bacterially-derived minicells are produced from a strain, including, but not limited to a strain of *Escherichia coli, Bacillus* spp., *Salmonella* spp., *Listeria* spp., *Mycobacterium* spp., *Shigella* spp., or *Yersinia* spp. In some embodiments, the bacterially-derived minicells are produced from a strain that naturally produces minicells. Such natural minicell producing strains produce minicells, for example, at a 2:1 ratio (2 bacterial cells for every one minicell) In certain embodiments, exemplary bacterial strains that naturally produce minicells include, but are not limited to *E. coli* strain number P678-54 CGSC number: 4928. *B. subtilis* designated number A18197, 168 strain CU403. In certain embodiments, minicells are produced by overexpressing certain proteins in bacteria, which proteins cause or increase minicell production (e.g., ftsZ protein).

As used herein, the term "display" refers to the exposure of the polypeptide of interest on the outer surface of the minicell. By way of non-limiting example, the displayed polypeptide may be protein or a protein domain which is either expressed on the minicell membrane or is associated with the minicell membrane such that the extracellular domain or domain of interest is exposed on the outer surface of the minicell (expressed and displayed on the surface of the minicell or expressed in the parental cell to be displayed on the surface of the segregated/budded minicell). In all instances, the "displayed" protein or protein domain is available for interaction with extracellular components. A membrane-associated protein may have more than one extracellular domain, and a minicell of the invention may display more than one membrane-associated protein.

As used herein, the terms "polypeptide", "protein" and "protein domain" refer to a macromolecule made up of a single chain of amino acids joined by peptide bonds. Polypeptides of the invention may comprise naturally occurring amino acids, synthetic amino acids, genetically encoded amino acids, non-genetically encoded amino acids, and combinations thereof. Polypeptides may include both L-form and D-form amino acids.

As used herein, the term "biologically active polypeptide" refers to a polypeptide which encodes a biologically functional protein. The term "biologically active polypeptide"

includes fusion proteins which perform a biological function. Exemplary biologically active polypeptides, include enzymes/enzyme moiety (e.g. wild type, variants, or engineered variants) that specifically bind to certain receptors or chemical substrates to effect a biological function such as biological signal transduction or chemical inactivation.

In certain embodiments, the biologically active polypeptide comprises a fusion protein. In certain embodiments, the fusion protein comprises at least one surface-expressing moiety, and at least one enzyme moiety.

Biologically active polypeptides that are within the scope of the present invention include, but are not limited to, enzymes/enzyme moieties such as hydrolases, lipases, phospholipases, transacylases, transaminases, pectinase, proteases, amylases, cellulases, cutinases, esterases, acylases, invertases, isomerases, lyases, glucosidases, oxidoreductases, transferases, ligases, amidases, manganese peroxidase, laccase, lignin peroxidase, horseradish peroxidase or phosphonate dehydrogenase, cytosolic aldehyde oxidase, carbaryl hydrolases, and amidases, HCH dehydrochlorinase, haloalkane dehalogenase, pyrethroid hydrolases (PytH, EspA) and permethrinase. In certain embodiments, the biologically active polypeptides displayed by the minicells of the invention comprise an organophosphate hydrolase. Exemplary organophosphate hydrolases that are within the scope of the invention include, but are not limited to sequences corresponding to Genbank Accession Nos. KM076938.1, KC562907.1, M29593.1. Organophosphate hydrolase targets the phosphorous ester bond of organophosphate pesticides leading to degradation of the pesticide into inert byproducts (e.g., two smaller inert by-products). In certain embodiments, the organophosphate hydrolase is selected from the group consisting of phosphotriesterases, methyl parathion hydrolases, and organophosphorus acid anhydrolases. In certain embodiments, the enzyme is fused to surface-expressing moiety. Exemplary surface-expressing moieties include but are not limited to ice nucleation protein (INPNC) or an exported bacterial protein. "Exported bacterial proteins," generally refers to bacterial proteins that are transported across the plasma membrane and function as an anchor for membrane proteins. Exemplary exported bacterial proteins encompassed by the present invention, include, but are not limited to LamB, OprF, OmpA, Lpp, MalE, PhoA, Bla, F1 or M13 major coat, and F1 or M13 minor coat.

As discussed above, in certain embodiments, the invention provides a composition comprising minicells which further comprise a second polypeptide displayed on the surface of the bacterial minicell, to increase adhesion to plants. Exemplary proteins or protein domains that mediate increased adhesion to plants include, but are not limited to cellulose binding domain (CBD). CBDs have been shown to bind tightly and rapidly to cellulose fibers, and thus enable strong attachment of the minicell compositions provided by the present invention to plants for efficient degradation of organophosphates. Exemplary CBD sequences that are within the scope of the invention include, but are not limited to sequences corresponding to Genbank Accession No. AB021656.1.

As used herein, the term "pesticide" refers to any substance used to kill, repel, or control certain forms of plant or animal life that are considered to be pests. Pesticides include herbicides for destroying weeds and other unwanted vegetation, insecticides for controlling a wide variety of insects, fungicides used to prevent the growth of molds and mildew, disinfectants for preventing the spread of bacteria, and compounds used to control mice and rats."

Pesticides within the scope of the present invention include, but are not limited to the classes of organophosphates, glyphosates (degraded using e.g., ligninolytic enzymes: manganese peroxidase, laccase, lignin peroxidase, horseradish peroxidase or phosphonate dehydrogenase), neonicotinoids (degraded using e.g., nitroreductases such as cytosolic aldehyde oxidase), carbamates (degraded using e.g., methyl carbamate-degrading hydrolases, carbaryl hydrolases, and amidases to degrade them), organochlorines (degrading using e.g., monooxygenases, HCH dehydrochlorinase, haloalkane dehalogenase), and pyrethroids (degraded using e.g., pyrethroid hydrolases (PytH, EspA) and permethrinase). Additional classes of pesticides within the scope of the present invention, include, but are not limited to stribilurins, anilenes, thiophthlamadies (Captan), aromatic hydrocarbons, nitriles, cyanoimidazoles, demethylation inhibitors, phenylpyrroles, carboximides, phosphonates, dicarboximides, phenylamides, polyoxins, benzimidazoles, aryloxyphenoxy propionates, cyclohexanediones, phenylpyrazolin, imidazolinones, sulfonylamino-carbonyltriazolinones, amides, sulfonylureas, pyraxoles, triazolpyramidines, triazolones, dinitroanilines, benzoic acids, carboxylic acids, piconolinic acids, phenoxys, phenyl-carbamates, triazines, triazinones, uracils, benzthiadiazoles, ureas, thiocarbamates, triazoles, aryl triazones, chloroacetamides, pyrazoles, benzofuranyl alkylsulfonates, semicarbazones, bipyridyliums, benzopyrazoles.

As used herein, the term "organophosphate pesticide" refers to a pesticide belonging to class of compounds which are esters of phosphoric acid, and have the following general chemical structure:

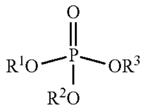

Organophosphates function by inhibiting the acetylcholinesterase of many living organisms, including human beings. High-level exposure to organophosphates results in acetylcholine accumulation, which interferes with muscular responses and leads to serious damage of vital organs and eventually death. Organophosphates within the scope of the present invention include, but are not limited to paraoxon, malathion, parathion, diazinon, naled, fenthion, dichlorvos, chlorpyrifos, phosmet, acephate, ethion, soman, sarin, tabun, VX, echothiophate, isoflurophate, trichlorfon, tetrachlorvinphos, azamethiphos, and azinphos-methyl.

In certain aspects, the present invention provides bacterial host cells that naturally produce minicells comprising one or more plasmid constructs for expression of one or more proteins within the same host cells. An expression construct may drive expression of a single protein, or multiple proteins under the expression of a single promoter (e.g., to produce a fusion protein), or multiple promoters. In some embodiments, one or more of the proteins can be expressed on the surface of the host cells, and the minicells produced by them. Expression of the protein(s) of interest can be driven by one or more promoters, including but not limited to inducible promoters. In certain aspects, the present invention provides minicell-producing host cells comprising an expression construct, wherein the expression construct comprises a gene that causes or enhances the production of minicells operably linked to expression sequences that are inducible, and wherein induction of the gene causes or enhances the production of minicells. In some embodiments, the minicell-producing host cells, include, but are not limited to a bacterial strain of *Escherichia coli, Bacillus* spp., *Salmonella* spp., *Listeria* spp., *Mycobacterium* spp., *Shigella* spp., or *Yersinia* spp. In some embodiments, the gene that causes or enhances the production of minicells, includes, but is not limited to, the tubulin-homolog ftsZ, and the inducible expression sequences can include, but are not limited to isopropyl □-D-1-thiogalactopyransoide (IPTG) inducible sequences (e.g., promoter from the lac operon). Additional exemplary prokaryotic promoters, which can be regulated (e.g., induced and/or repressed), and are within the scope of the present invention are shown in Table 1. In certain aspects, the expression construct further comprises nucleic acid sequences encoding a reporter polypeptide or amino acid sequence for monitoring, visualizing, or assaying protein expression and/or minicell formation. In some embodiments, the reporter polypeptides or amino acid sequences, includes, by way of non-limiting example, a green fluorescent protein (GFP), a luciferase, a beta-galactosidase, a His tag, an epitope, or a biotin-binding protein such as streptavidin or avidin.

TABLE 1

| Promoter | Primarily Used For | Description | Expression | Additional Considerations |
|---|---|---|---|---|
| T7 | In Vitro transcription/general expression | Promoter from T7 bacteriophage | Constitutive, but requires T7 RNA polymerase | Can be used for in vitro transcription only if 2 different phage promoters are present in opposite orientations to the gene |
| T7lac | High levels of gene expression | Promoter from T7 bacteriophage plus lac operators | Negligible basal expression when not induced. Requires T7 RNA polymerase, which is also controlled by lac operator. Can be induced by IPTG | Commonly found in pET vectors. Very tightly regulated by the lac operators. Good for modulating gene expression through varied inducer concentrations. |
| Sp6 | In vitro transcription/general expression | Promoter from Sp6 bacteriophage | Constitutive, but requires SP6 RNA polymerase | Can be used for in vitro transcription only if 2 different phage promoters are present in opposite orientations to gene |
| Trp | High levels of gene expression | Promoter from *E. coli* tryptophan operon | Repressible | Gets turned off with high levels of cellular tryptophan |
| Lac | General Expression | Promoter from lac operon | Constitutive in the absense of lac repressor (lacI or lacIq). Can be induced by IPTG or lactose. | Leaky promoter with somewhat weak expression. LacIq mutation increases expression of the repressor 10x, thus tightening regulation of lac promoter. Good for modulating gene expression through varied inducer concentrations. |
| Ptac | General Expression | Hybrid promoter of lac and trp | Regulated like the lac promoter | Contains -35 region from trpB and -10 region from lac. Very tight regulation. Good for modulating gene expression through varied inducer concentrations. Generally better expression than lac alone. |
| pL | High levels of gene expression | Promoter from bacteriophage lambda | Can be temperature regulatable | Often paired with the temperature sensitive cl857 repressor |
| araBAD | General Expression | Promoter of the arabinose metabolic operon | Inducible by arabinose and repressed catabolite repression in the presence of glucose or by competitive binding of the anti-inducer fucose | Weaker. Commonly found in pBAD vectors. Good for rapid regulation and low basal expression; however, not well-suited for modulating gene expression through varied inducer concentrations |

In certain aspects, the present invention provides a method for making minicells, the method comprising (a) culturing a minicell-producing parent cell, wherein the parent cell comprises an expression construct, wherein the expression construct comprises a ftsZ gene operably linked to an IPTG-inducible sequence, and wherein induction of the ftsZ gene causes or enhances the production of minicells; and (b) separating the minicells from the parent cell, thereby generating a composition comprising minicells. In certain embodiments, the method further comprises (c) purifying the minicells from the composition by centrifugation and/or filtration. In certain embodiments, one or more additional expression constructs can be introduced into the minicell-producing parent cell which comprise ftsZ gene. In such instances, the expression constructs may be simultaneously or sequentially introduced into the parent cell prior to induction for minicell formation, and can comprise one or more selection markers (e.g., antibiotic resistance genes) and/or reporter genes to allow for selection and/or visualization of minicells expressing the protein(s) of interest. In certain embodiments, the ftsZ expression construct can express one or more additional proteins, which are driven by the same or different promoters, including inducible promoters.

In certain aspects, the present invention provides a method for making minicells, the method comprising (a) culturing a minicell-producing parent cell, wherein the parent cell comprises at least one expression construct, wherein the at least one expression construct comprises a gene encoding a biologically active polypeptide operably linked to an IPTG-inducible sequence, and wherein induction causes expression of the biologically active polypeptide; and (b) separating the minicells from the parent cell, thereby generating a composition comprising minicells. In certain embodiments, the method further comprises (c) purifying the minicells from the composition by centrifugation and/or filtration. In certain embodiments, the parent cell is a bacterial strain that naturally produces minicells. In certain embodiments, the gene is INPNC-OPH, which encodes organophosphate hydrolase (OPH) fused to an ice nucleation protein (INPC). In certain embodiments, the minicell-producing parent cell can contain more than one expression construct. In such instances, the parent cell may comprise more than one expression construct which are introduced either simultaneously or sequentially into the parent cell, and can comprise one or more selection markers (e.g., antibiotic resistance genes) and/or reporter genes to allow for selection and/or visualization of minicells expressing the protein(s) of interest.

In certain embodiments, the invention provides minicells having about 90-99% purity, or about 90-95%. Purity refers to the absence of contaminating parental bacteria in the composition. Minicells can be separated from their parent cells based on their much smaller size. The minicells provided by the present invention are typically about 0.4 μm-0.5 μm in diameter. In certain embodiments, the composition comprises an aqueous solution of minicells (e.g., *E. coli* minicells) at a concentration from about $1\times10^6$ to about $1\times10^9$ cells/mL. In certain embodiments, the minicell solution is prepared in water containing 0.5% zinc (a co-factor for OPH), and applied to the crop or agricultural product using a spray bottle.

In certain aspects, the invention provides a method for pesticide degradation, the method comprising contacting a crop or an agricultural product with any of the compositions of the invention disclosed herein, wherein the composition mediates degradation of the pesticide to yield inert by-products. In certain embodiments, pesticide degradation can be evaluated by measuring the levels of one or more by-products.

In other embodiments, pesticide degradation can be evaluated by measuring the amount of residual pesticide. In addition, or alternatively, the half-life of the pesticide may be used to measure the efficacy of any of the compositions of the invention disclosed herein. The half-life is the time it takes for a certain amount of a pesticide to be reduced by half. In general, a pesticide will break down to 50% of the original amount after a single half-life. After two half-lives 25% will remain. In some embodiments, the half-life of the pesticide may be reduced by a factor of about 2, about 3, about 4, about 5, about 6, about 7, about 8, about 9, about 10, about 20, about 30, about 40, or about 50 or more. In certain embodiments, invention provides a method for reducing the half-life of a pesticide (e.g., organophosphate pesticide). In certain embodiments, the invention provides a method for reducing the half-life of malathion. In certain embodiments, the half-life of malathion is reduced to less than 4 hours (<4 h.).

In certain aspects, the invention provides a method for bioremediation, the method comprising contacting a crop or an agricultural product with any of the compositions of the invention disclosed herein the composition mediates degradation of the pesticide to yield inert by-products.

EXAMPLES

The invention is now described with reference to the following Examples. These Examples are provided for the purpose of illustration only, and the invention is not limited to these Examples, but rather encompasses all variations which are evident as a result of the teachings provided herein.

Example 1

Construction of an IPTG-Inducible ftsZ Operon for the Production of *E. coli* Minicells Despite many attractive qualities for synthetic biology, *Escherichia coli* and other engineering-amenable bacteria suffer from a number of inherent biosafety issues that limit their practical application. A safer alternative exists in the little-known nano-chassis called a minicell—the anucleoid product of an aberrant, asymmetric cell division. To introduce minicells to synthetic biology, a minicell-inducing operon from standardized parts was engineered. Through IPTG-tunable overexpression of the tubulin-homolog FtsZ, this operon enables optimization of *E. coli* minicell production. Whereas a spatially oscillating "Z ring" composed of FtsZ protein marks cleavage at the cell midline in wild type *E. coli*, overexpression of FtsZ initiates Z-ring assembly distal to the midline to form a minicell (FIG. 1). These engineered minicells are achromosomal bacterial particles that are unable to replicate and cause infection or ecological harm.

Synthesis and Cloning of ftsZ: Integrated DNA Technologies (Coralville, Iowa, USA) synthesized the coding sequence of the ftsZ gene based on NCBI database sequence 944786 flanked by the BioBrick prefix (gaattcgcggccgcttctag; SEQ ID NO: 1) and suffix (tactagtagcggccgctgcag; SEQ ID NO: 2). Prior to synthesis, the sequence was codon optimized to remove an EcoRI restriction site 112 bp 3' of the start site. The synthesized ftsZ gene was cloned into the vector pSB1C3 (Registry of Standard Biological Parts, iGEM Foundation, Cambridge, Mass., USA) using EcoRI and PstI restriction sites, forming construct BBa_K1011000. Using primers VF2 (tgccacctgacgtctaagaa; SEQ ID NO: 3) and VR (attaccgcctttgagtgagc; SEQ ID NO: 4), the sequence identity was validated by DNA sequencing and comparison to a ftsZ reference sequence (NCBI Accession No. 944786).

Formation of IPTG-Inducible ftsZ Operon: To construct an IPTG-inducible operon that contains, in order, ftsZ and GFP, an EcoRI-SpeI fragment containing BioBrick BBa_S05213 was cloned into the EcoRI and XbaI restriction sites that are 5' of BioBrick BBa_S05212 in vector pSB1C3, forming BioBrick BBa_K1011001. To construct BioBrick BBa_S05212 (875 bp), an EcoRI-SpeI fragment containing BioBrick BBa_S05211 was cloned into the EcoRI and XbaI restriction sites that are 5' of a double terminator sequence (BioBrick BBa_B0015) in vector pSB1AK3. BioBrick BBa_S05212 was subsequently cloned into pSB1C3 using EcoRI and PstI restriction sites. To construct BioBrick BBa_S05211 (738 bp), an XbaI-PstI fragment containing GFP coding sequence (BioBrick BBa_E0040) was cloned into the SpeI and PstI restriction sites that are 3' of the RBS sequence (BioBrick BBa_B0034) in vector pSB1A3. To construct BioBrick BBa_S05213 (1233 bp), an XbaI-PstI fragment containing ftsZ coding sequence (BioBrick BBa_K1011000) was cloned into the SpeI and PstI sites 3' of an IPTG-inducible promoter and a RBS (BioBrick BBaK215000) in vector pSB1A3. Using primers VF2 and VR, the sequence of each construct was validated before submission to the Registry of Standard Biological Parts (iGEM Foundation, Cambridge, Mass.).

Reagents and Culturing of *E. coli*: Transformed XL1-Blue *E. coli* were cultured at 37° C. in Luria Broth (LB) with antibiotics as appropriate (chloramphenicol 25 mg/L, ampicillin 100 mg/L, or kanamycin 50 mg/L). Competent cells were obtained from Sigma (St. Louis, Mo., USA). Restriction and DNA modifying enzymes were obtained from New England BioLabs, Inc. (Ipswich, Mass., USA).

Microscopy: Cells transformed with BioBrick BBa_K1011001 in pSB1C3 were incubated in LB medium with or without 40 μM IPTG for 14 h prior to microscopy. Images were acquired at 400× total magnification using an Olympus BX50 microscope with Olympus DP25 camera attachment, Scion Image software (Scion Corporation, Frederick, Md., USA), and 40× Olympus UPlanFL objective.

Minicell Purification: Minicells were purified by differential centrifugation at 2,000 g for 10 min at 4° C. to pellet the parent bacteria followed by centrifugation of the supernatant at 10,000 g for 10 min at 4° C. to pellet minicells. The minicell pellet was then re-suspended in 50 mL LB and incubated at 37° C., 180 rpm for 90 min with 100 mg/L ceftriaxone. This dose of ceftriaxone is sufficient to cause cell lysis without having any detrimental effect on minicell integrity. The resulting minicell preparation was filtered at room temperature through a 0.45 μm dead end filter (Millipore SE1M003M00) to remove any remaining parent cells, followed by additional filtration with a 0.22 μm cross-flow filter (Millipore GVWP04700) to remove small cell debris and endotoxins.

Figure 2B:
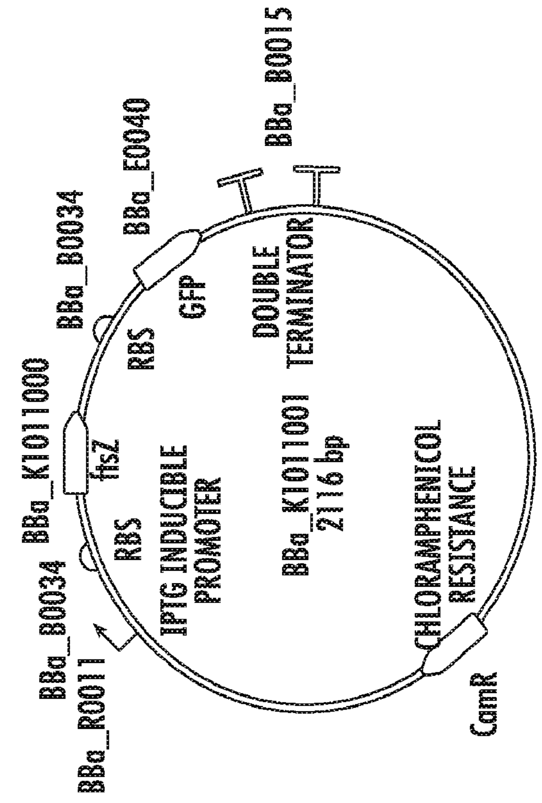
FIGS. 2A-2B: Construction of an exemplary bacterial minicell-inducing plasmid.
Figure 2A:
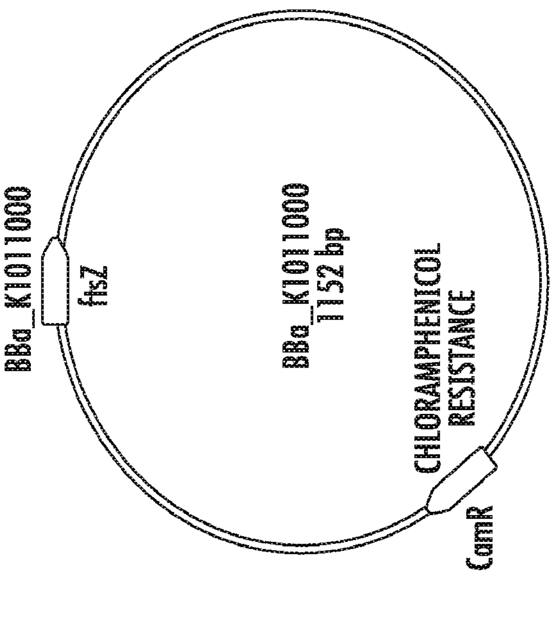

To facilitate the production of minicells two plasmid constructs were designed containing either (1) the ftsZ gene alone (FIG. 2A), or (2) an operon consisting of an IPTG-inducible ftsZ gene and Green Fluorescent Protein (GFP) reporter gene (FIG. 2B). The first construct (BBa_K1011000) served as an intermediary for the production of the second construct. Here, this first construct is made available to the synthetic biology community because this copy of ftsZ lacks an internal EcoRI restriction site and is thus compatible with standardized DNA assembly methods. The second construct (BBa_K1011001) was used for the production of minicells and contains an operon with two genes, ftsZ, which, when overexpressed, drives minicell formation, and GFP. GFP expression serves as a reporter for the transcriptional expression of ftsZ and enables easy visualization of cells transformed with this construct.

Figure 3:
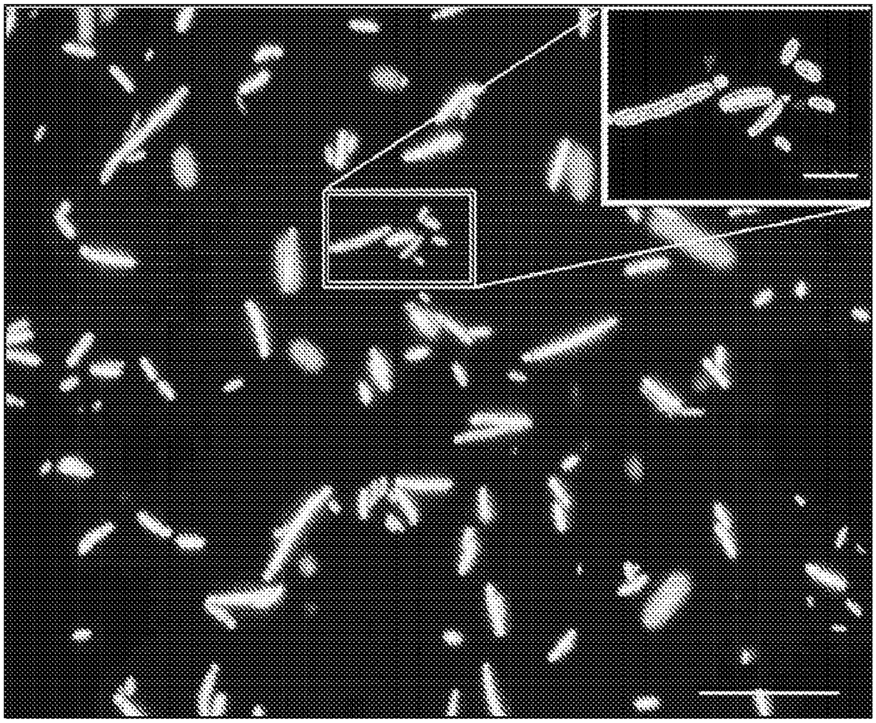
FIG. 3: Fluorescence microscopy visualization of BBa_K1011001-transformed XL1-Blue *E. coli* cells grown in the presence of 40 μM IPTG. As shown in the inset and marked by the red triangles, asymmetric cell division successfully produced minicells after 14 h of induction. Scale bar is 35 μm and inset scale bar is 9 μm.
Figure 4:
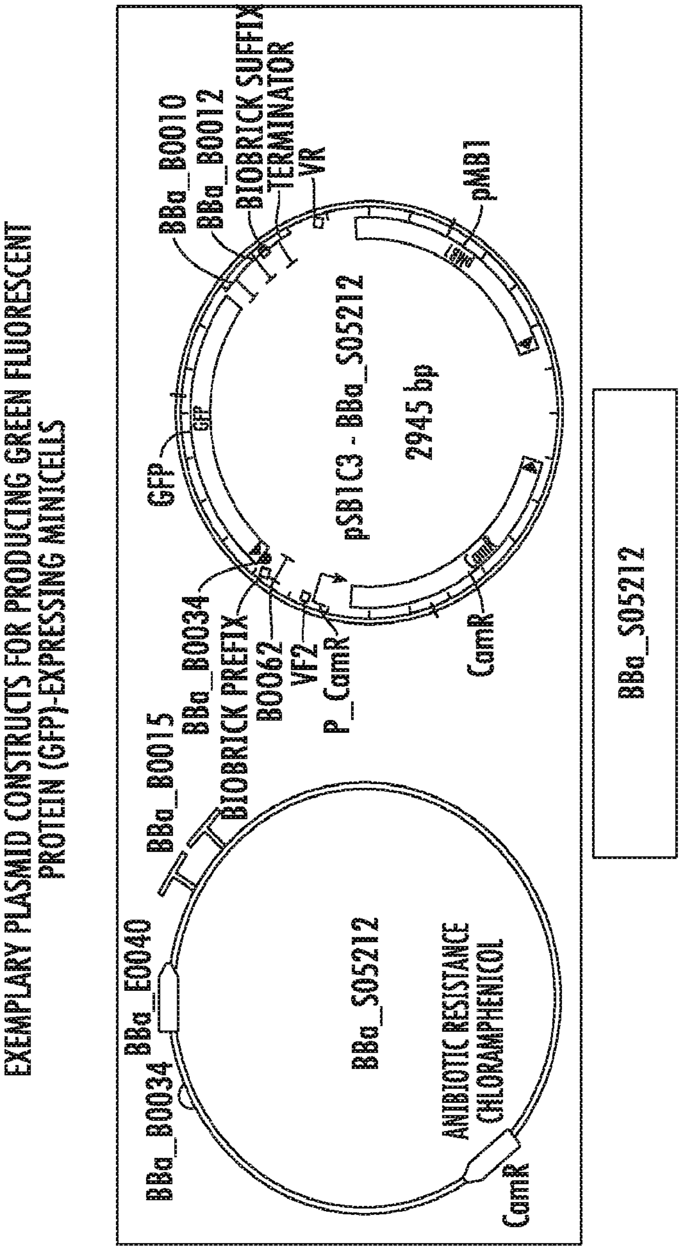
FIG. 4: Exemplary plasmid constructs for producing green fluorescent protein (GFP)-expressing minicells.
Figure 5A:
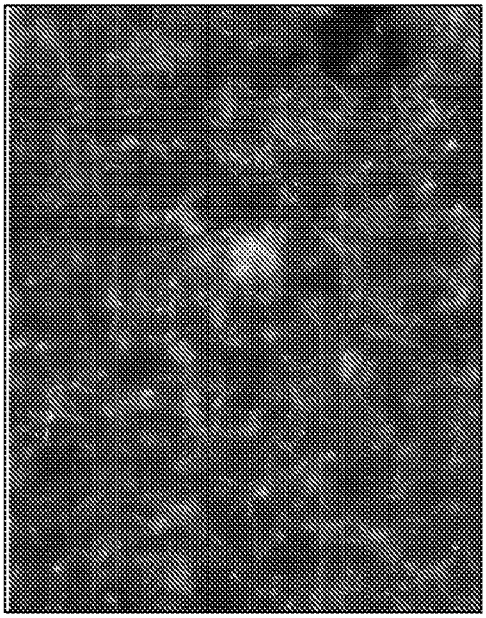
FIGS. 5A-5B: Fluorescence microscopy visualization of induction of minicell formation and purified minicells.
Figure 5B:
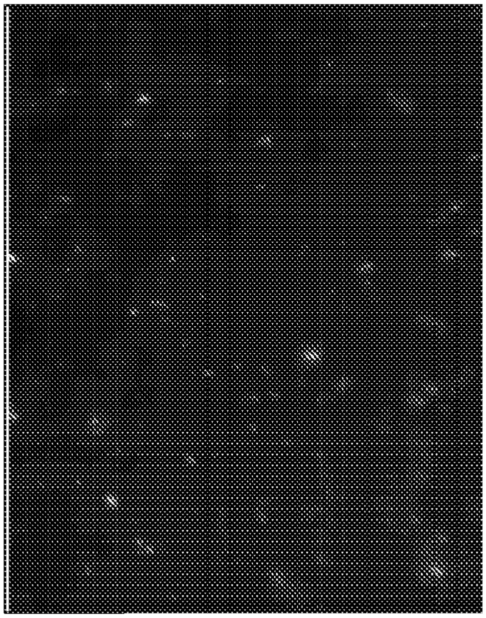
Figure 6A:
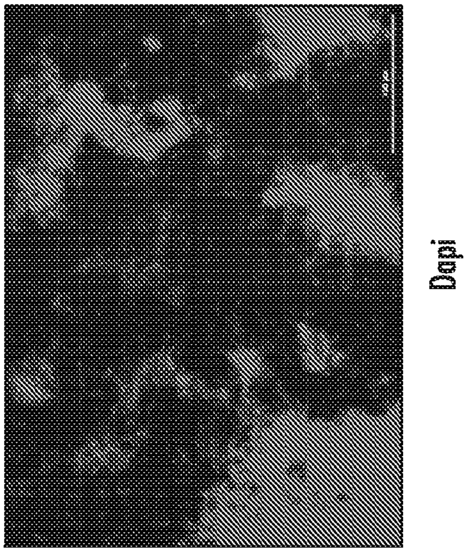
FIGS. 6A-6C: Fluorescence staining demonstrating that minicells lack DNA but retain membrane proteins. The mixed solution of *E. coli* and minicells were stained with DAPI (FIG. 6A); DAPI and GFP (FIG. 6B), and the resulting fluorescent photographic images were overlapped to visualize and identify cells that were green but lacked the blue staining (FIG. 6C), which correspond to the minicells.
Figure 6B:
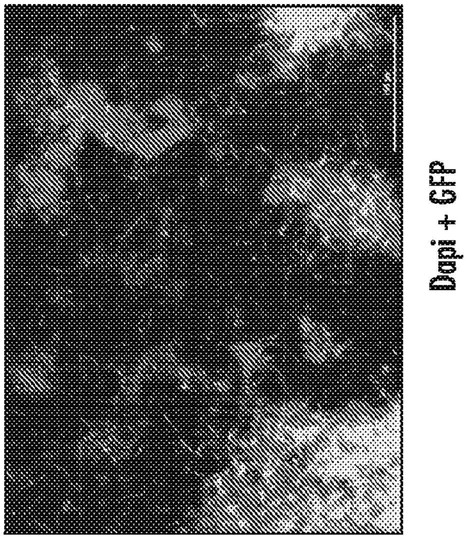
Figure 6C:
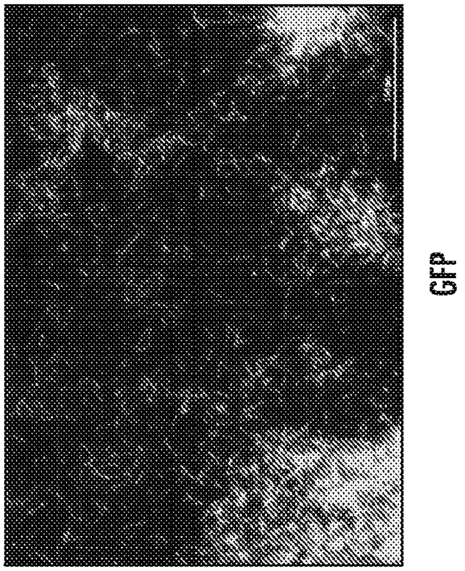

To test the functionality of the minicell-producing construct, XL1-Blue *E. coli* cells were transformed with BBa_K1011001. As shown in FIG. 3, fluorescence microscopy revealed minicell production 14 h post-induction with 40 μM IPTG. Elongated, rod-shaped cells were also observed as a byproduct of multiple rounds of asymmetric cell division. As expected, minicell production occurred post-IPTG induction, and GFP provided a visual readout of induction and aided minicell detection.

Example 2

Figure 7B:
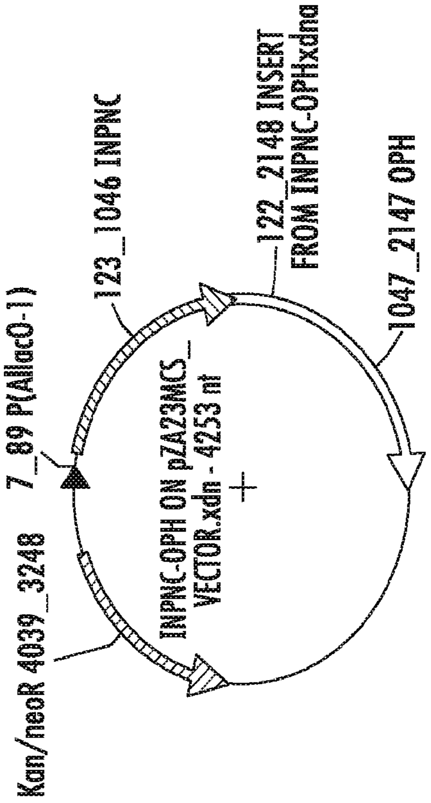
FIGS. 7A-7B: Exemplary plasmid construct for surface expression of organophosphate hydrolase (OPH).
Figure 7A:
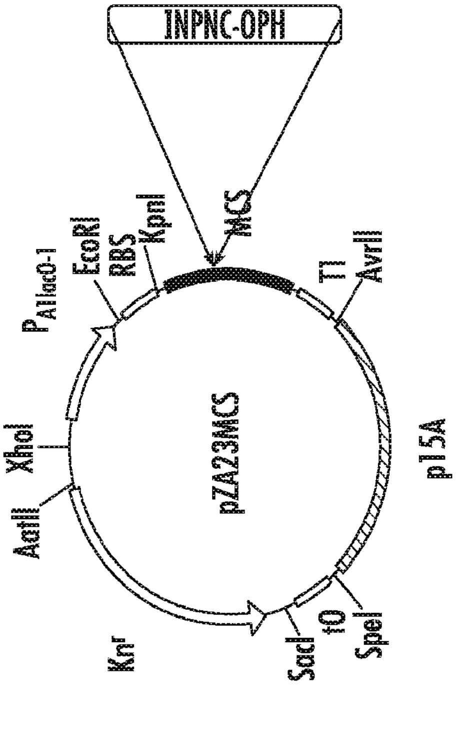
Figure 8:
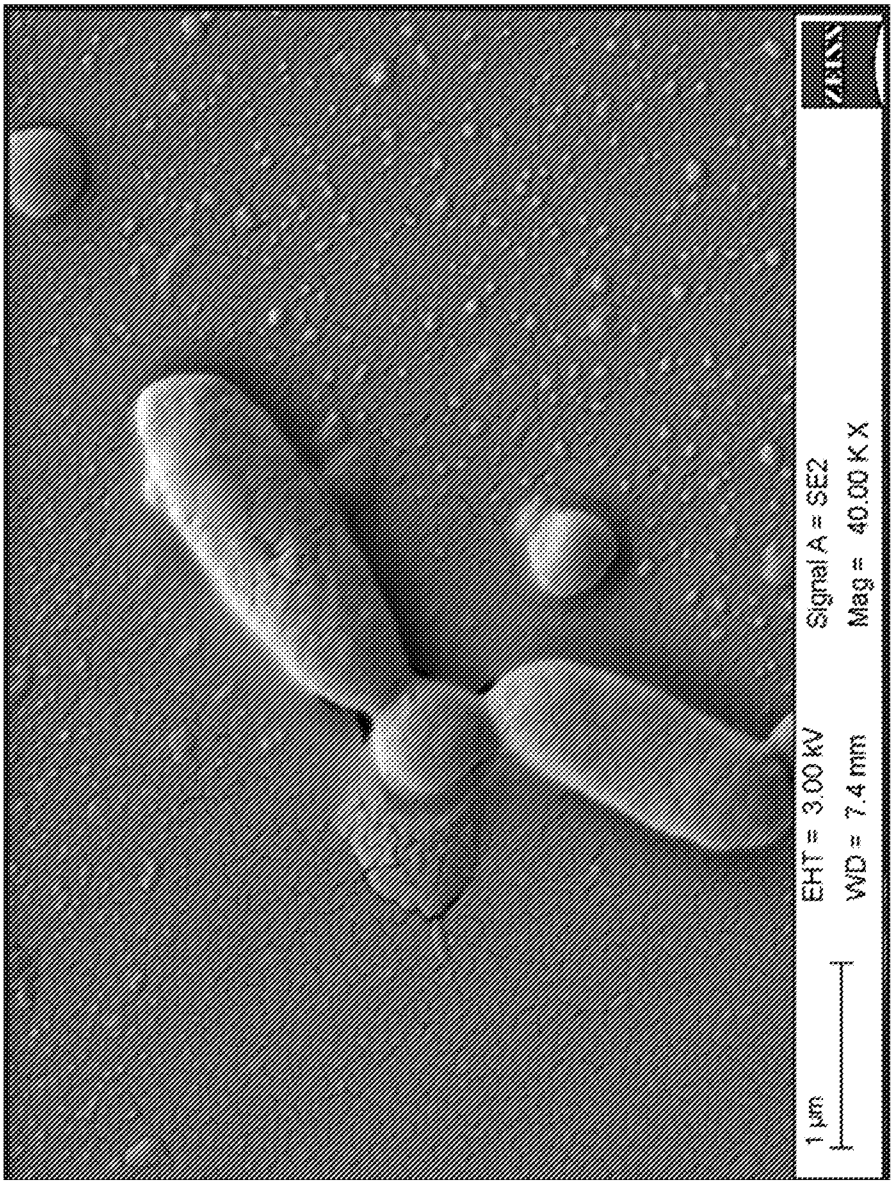
FIG. 8: Scanning electron micrograph showing minicell formation in *E. coli.*
Figure 9A:
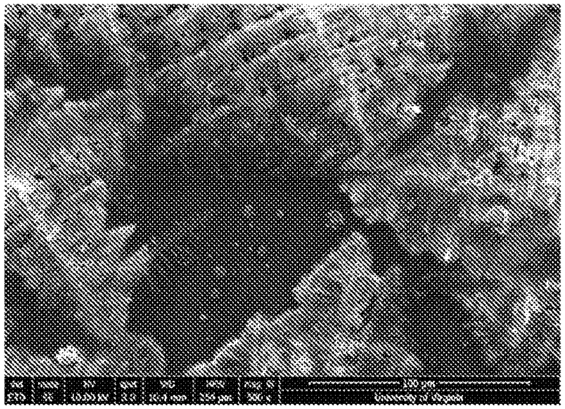
FIGS. 9A-9C: Determination of minicell size.
Figure 9B:
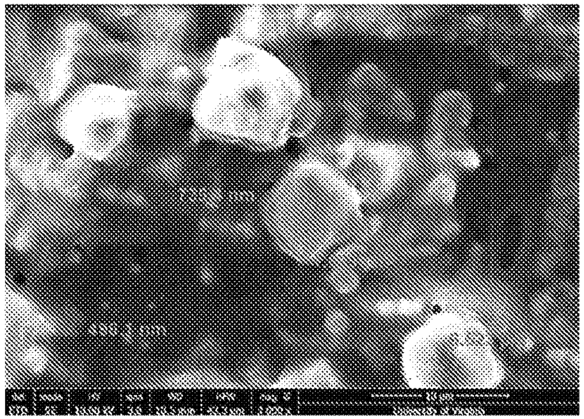
Figure 9C:
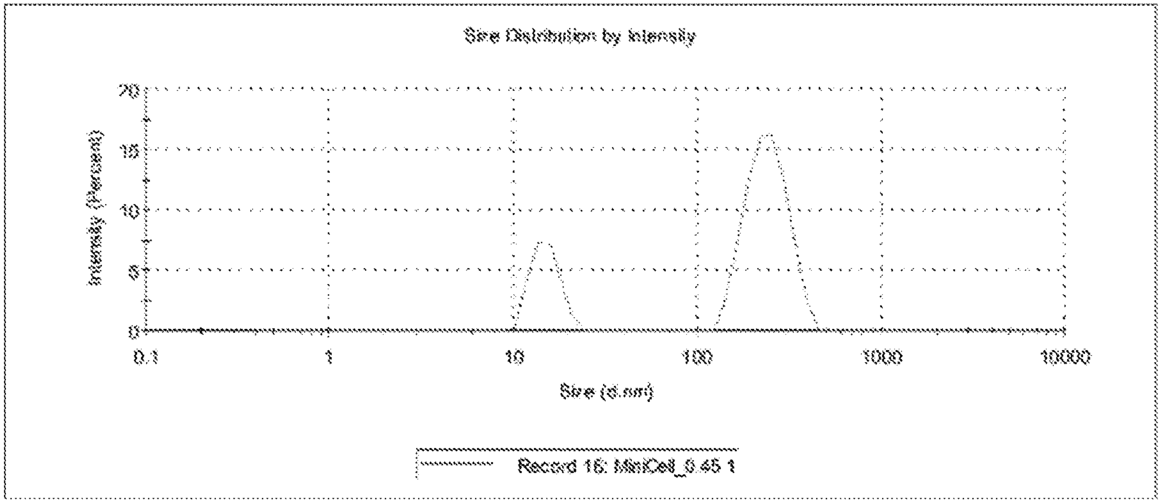

Plasmid Construct for Surface Expression of Organophosphate Hydrolase (OPH) on Minicells An exemplary plasmid construct for surface expression of organophosphate hydrolase (OPH) on minicells is shown in FIGS. 7A-7B. The $Kn^r$ designation represents the kanamycin resistance gene used in order to ascertain whether isolated minicells expressed OPH; any minicell lacking the plasmid would die upon exposure to sufficient levels of kanamycin. The $P_{AllacO\text{-}1}$ designation represents the lac promoter that regulates the expression of our INPNC-OPH protein. In the absence of IPTG, expression of the INPNC-OPH protein will be actively repressed until IPTG is in solution. The p15A represents the origin of replication of the plasmid. This allows for the plasmid to be copied within the cell in order to ensure that maximal expression of the desired protein—INPNC-OPH—upon induction with IPTG. The INPNC-OPH gene codes for organophosphate hydrolase fused to an ice nucleation protein. The ice nucleation protein allows the OPH to be expressed on the surface of an *E. coli* parent cell and thus on the surface of a resultant *E. coli* minicell.

Example 3

Induction and Purification of Minicells

Bacterial strains that naturally produce minicells (commonly at a 2:1 ratio (2 bacterial cells for every one minicell) were used to obtain OPH-expressing minicells (produced using the construct shown in FIGS. 7A-7B and described in Example 2). Minicells were purified by differential centrifugation at 2,000 g for 10 min at 4° C. to pellet the parent bacteria followed by centrifugation of the supernatant at 10,000 g for 10 min at 4° C. to pellet minicells. The minicell pellet was then re-suspended in 50 mL LB and incubated at 37° C., 180 rpm for 90 min with 100 mg/L ceftriaxone. This dose of ceftriaxone is sufficient to cause cell lysis without having any detrimental effect on minicell integrity. The resulting minicell preparation was filtered at room temperature through a 0.45 μm dead end filter (Millipore SE1M003M00) to remove any remaining parent cells, followed by additional filtration with a 0.22 μm cross-flow filter (Millipore GVWP04700) to remove small cell debris and endotoxins.

Example 4

Degradation of Paraoxon (Organophosphate) by Minicells Expressing/Displaying Organophosphate Hydrolase (OPH) on their Surface.

Figure 10A:
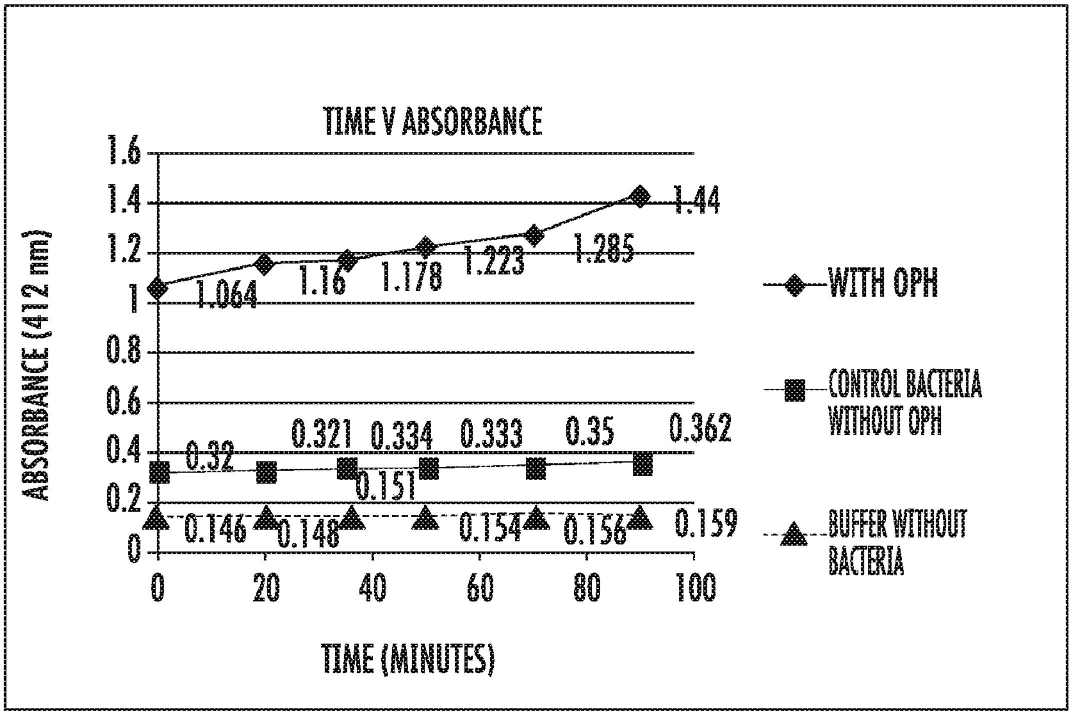
FIGS. 10A-10B: Breakdown of organophosphate (paraoxon) by minicells (produced using the plasmid construct shown in FIGS. 7A-7B) expressing organophosphate hydrolase (OPH) on their surface. Paraoxon is broken down into p-nitrophenol, a chromogenic product with absorbance at 412 nm. As illustrated by the graphs, the surface OPH-expressing minicells showed very efficient degradation compared to the controls.
Figure 10B:
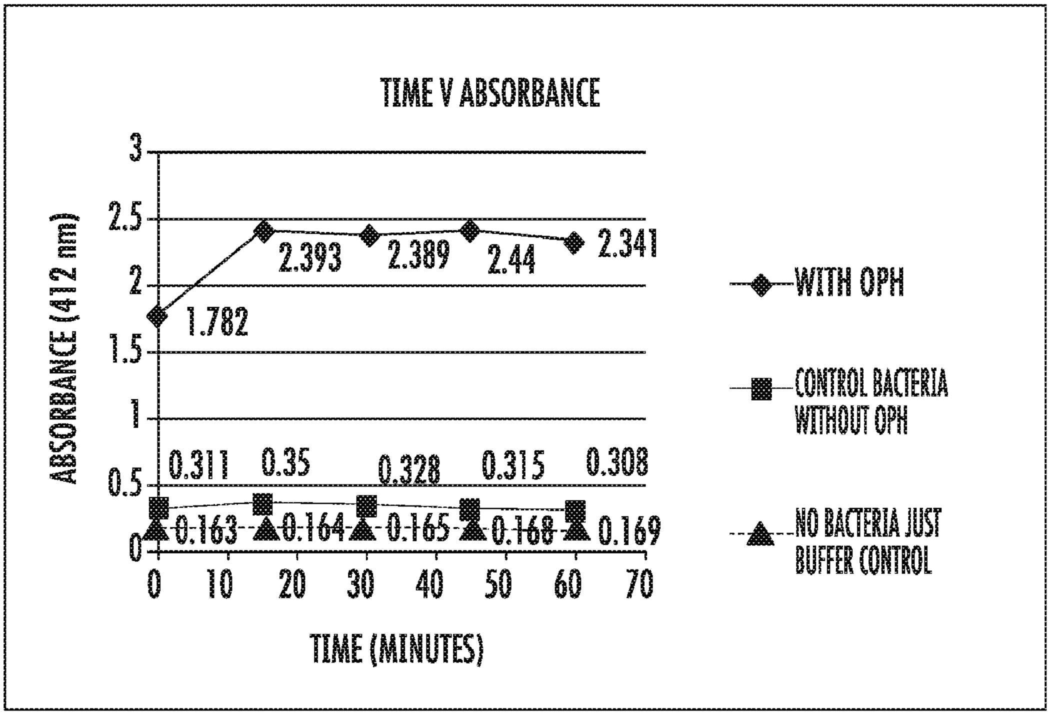

Degradation of paraoxon by the OPH-expressing minicells (produced using the construct shown in FIGS. 7A-7B and described in Example 2) was studied. The results are shown on FIGS. 10A-10B.

Example 5

Field Studies of Malathion Degradation by Minicells Expressing/Displaying Organophosphate Hydrolase (OPH) on their Surface.

Figure 11:
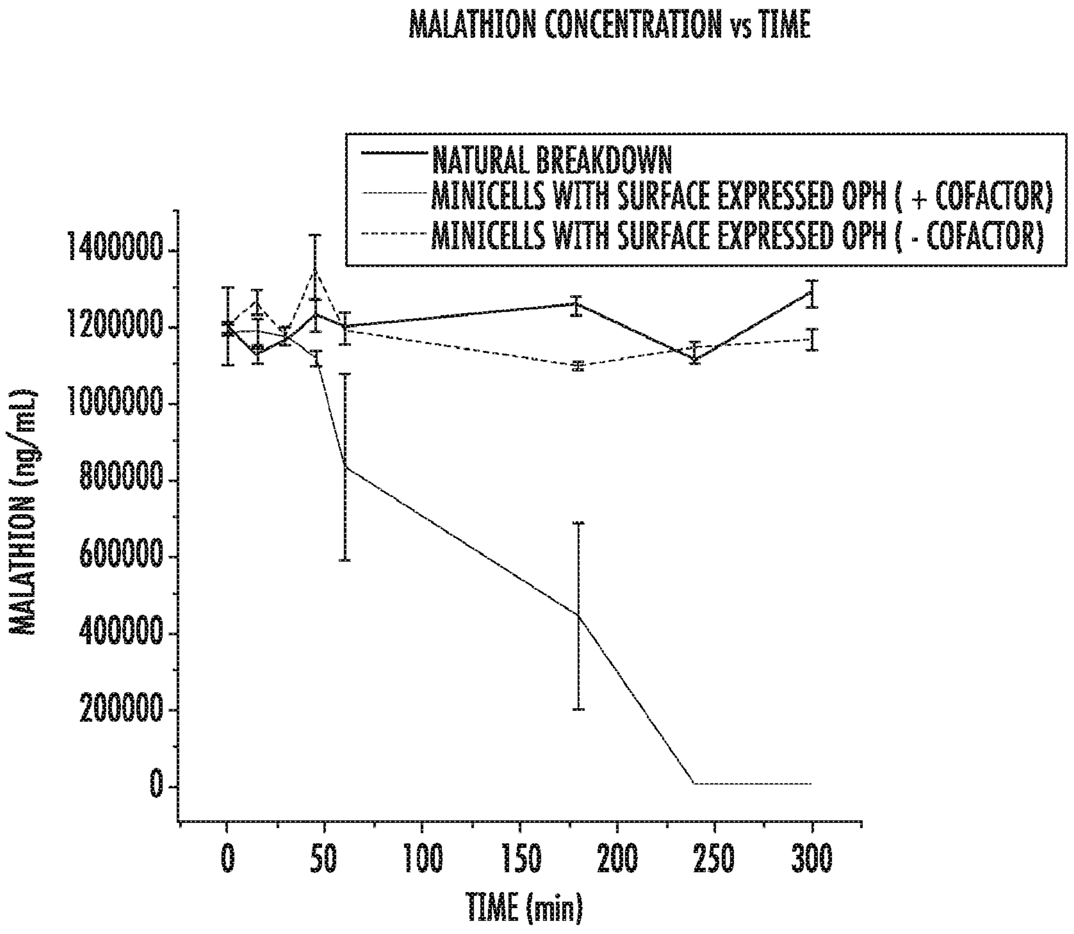
FIG. 11: Field data showing malathion concentration vs. time after an application of surface OPH-expressing *E. coli* minicells (produced using the plasmid construct shown in FIGS. 7A-7B). The graph depicted in FIG. 11 shows the decrease in concentration of the organophosphate class pesticide malathion over time after an application of minicells with a surface expressed organophosphate hydrolase to plants that had been sprayed with malathion. All data points were created by collecting leaves in triplicate and extracting malathion from the leaves on site at the appropriate time points. The extraction contained no water and was stored at −80° C. so any further breakdown of malathion was halted. These three experimental conditions were chosen in order to best isolate the action of the OPH enzyme on the minicells. The natural breakdown condition was chosen to demonstrate that this pesticide does not breakdown quickly on its own. The minicells with surface expressed OPH (without/(−) cofactor) was chosen as a condition to demonstrate that the solution containing the minicells without the enzyme's cofactor (zinc) are not functional and do not contribute to the reduction in malathion concentration. The minicells with surface expressed OPH (with/(+) cofactor) was our fully active solution. Each extraction was diluted into 3 aliquots and analyzed via LC/MS and the concentrations calculated from an internal malathion standard curve. The error bars were calculated from the standard error between data points corresponding to their respective time points with n=9. A t-test and ANOVA calculation on the data points revealed that there is no significant difference between the natural breakdown and minicells with surface expressed OPH (without/(−) cofactor), while there was a significant difference between both of those conditions and the minicells with surface expressed OPH (with/(+) cofactor).

A minicell solution prepared from purified *E. coli* minicells (e.g., as described in Example 3 above) The minicell solution comprises about $1\times10^6$ to about $1\times10^9$ minicells/milliliter of the solution. The minicell solution was prepared in water containing 0.5% zinc (the cofactor for OPH), and applied with a spray bottle to grapes grown in several vineyards. The application was performed once, but could be applied multiple times if necessary or desirable. In order to assay for pesticide degradation, samples of leaves, grapes, and runoff were collected at varying time points up to six hours (t=0 min, t=0.1 min, t=15 min, t=30 min, t=45 min, t=60 min, t=90 min, t=120 min, t=150 min, t=180 min, t=240 min, t=300 min, t=360 min), and the residual pesticide was extracted with ethyl acetate, and analyzed with mass spectrometry. The results of the study are shown in FIG. 11.

What is claimed is:

1. A composition comprising a plurality of intact, bacterially-derived minicells, wherein each minicell of said plurality comprises a biologically active polypeptide displayed on the surface of the bacterial minicell, wherein said biologically active polypeptide has pesticide degrading activity.

2. The composition of claim 1, wherein the bacterially-derived minicells are produced from a strain of *Escherichia coli, Bacillus* spp., *Salmonella* spp., *Listeria* spp., *Mycobacterium* spp., *Shigella* spp., or *Yersinia* spp.

3. The composition of claim 1, wherein the pesticide is selected from the group consisting of organophosphates, glyphosates, neonicotinoids, carbamates, organochlorines, pyrethroids, Stribilurins, anilenes, thiophthlamadies (Captan), aromatic hydrocarbons, nitriles, cyanoimidazoles, demethylation inhibitors, phenylpyrroles, carboximides, phosphonates, dicarboximides, phenylamides, polyoxins, benzimidazoles, aryloxyphenoxy propionates, cyclohexanediones, phenylpyrazolin, imidazolinones, sulfonyl aminocarbonyltriazolinones, amides, sulfonylureas, pyraxoles, triazolpyramidines, triazolones, dinitroanilines, benzoic acids, carboxylic acids, piconolinic acids, phenoxys, phenyl-carbamates, triazines, triazinones, uracils, benzthiadiazoles, ureas, thiocarbamates, triazoles, aryl triazones, chloroacetamides, pyrazoles, benzofuranyl alkylsulfonates, semicarbazones, bipyridyliums, and benzopyrazoles.

4. The composition of claim 1, wherein the pesticide is an organophosphate selected from the group consisting of paraoxon, malathion, parathion, diazinon, naled, fenthion, dichlorvos, chlorpyrifos, phosmet, acephate, ethion, soman, sarin, tabun, VX, echothiophate, isoflurophate, trichlorfon, tetrachlorvinphos, azamethiphos, and azinphos-methyl.

5. The composition of claim 4, wherein the pesticide comprises malathion.

6. The composition of claim 1, wherein the biologically active polypeptide comprises a fusion protein.

7. The composition of claim 6, wherein the fusion protein comprises at least one surface-expressing moiety, and at least one enzyme moiety.

8. The composition of claim 7, wherein the at least one surface-expressing moiety comprises an ice nucleation protein (INPNC) or an exported bacterial protein, including wild type or mutant versions thereof.

9. The composition of claim 8, wherein the exported bacterial protein is selected from the group consisting of LamB (λ receptor), OprF, OmpA (3a, II), Lpp (lipoprotein), MalE (maltose-binding protein), PhoA (alkaline phosphatase), Bla (TEM-1 β-lactamse, f1 or M13 major coat, f1 or M13 minor coat, and any wild type or mutant versions thereof.

10. The composition of claim 9, wherein said at least one enzyme moiety is selected from the group consisting of hydrolases, lipases, phospholipases, transacylases, transaminases, pectinase, proteases, amylases, cellulases, cutinases, esterases, acylases, invertases, isomerases, lyases, glucosidases, oxidoreductases, transferases, ligases, amidases, manganese peroxidase, laccase, lignin peroxidase, horseradish peroxidase or phosphonate dehydrogenase, cytosolic aldehyde oxidase, carbaryl hydrolases, and amidases, HCH dehydrochlorinase, haloalkane dehalogenase, pyrethroid hydrolases (PytH, EspA) and permethrinase.

11. The composition of claim 9, wherein said at least one enzyme moiety comprises an organophosphate hydrolase.

12. The composition of claim 11, wherein the organophosphate hydrolase is selected from the group consisting of phosphotriesterases, methyl parathion hydrolases, and organophosphorus acid anhydrolases.

13. The composition of claim 1, further comprising a second polypeptide displayed on the surface of the bacterial minicell, to increase adhesion to plants.

14. The composition of claim 13, wherein the second polypeptide comprises a fusion protein.

15. The composition of claim 14, wherein the fusion protein comprises at least one surface-expressing moiety and at least one plant cell adhesion moiety.

16. The composition of claim 15, wherein said at least one surface-expressing moiety comprises an exported bacterial protein selected from the group consisting of LamB (λ receptor), OprF, OmpA (3a, II), Lpp (lipoprotein), MalE (maltose-binding protein), PhoA (alkaline phosphatase), Bla (TEM-1 β-lactamse, f1 or M13 major coat, f1 or M13 minor coat and any wild type or mutant versions thereof.

17. The composition of claim 16, wherein said at least one plant cell adhesion moiety comprises a cellulose binding domain.

18. The composition of claim 1, wherein the minicells have at least 90-95% purity.

19. The composition of claim 1, wherein the minicells are about 0.4 μm-0.5 μm in diameter.

20. A method for pesticide degradation, the method comprising contacting a crop or an agricultural product with the composition of claim 1, wherein the composition mediates degradation of the pesticide to yield inert by-products.

* * * * *

UNITED STATES PATENT AND TRADEMARK OFFICE

CERTIFICATE OF CORRECTION

PATENT NO. : 10,913,940 B2
APPLICATION NO. : 16/092697
DATED : February 9, 2021
INVENTOR(S) : Payam Pourtaheri et al.

It is certified that error appears in the above-identified patent and that said Letters Patent is hereby corrected as shown below:

On the Title Page

Item (72) Inventors, please correct the spelling of the seventh inventor's name as it appears below:
-- Andrei KHOKHLATCHEV Charlottesville, VA --

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*

```
                          SEQUENCE LISTING


<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: BioBrick prefix

<400> SEQUENCE: 1

gaattcgcgg ccgcttctag                                                 20


<210> SEQ ID NO 2
<211> LENGTH: 21
<212> TYPE: DNA
<213> ORGANISM: Artificial Sequence
<220> FEATURE:
<223> OTHER INFORMATION: BioBrick suffix

<400> SEQUENCE: 2

tactagtagc ggccgctgca g                                               21


<210> SEQ ID NO 3
<211> LENGTH: 20
<212> TYPE: DNA
<213> ORGANISM: Artificial Sequence
<220> FEATURE:
<223> OTHER INFORMATION: Primer VF2

<400> SEQUENCE: 3

tgccacctga cgtctaagaa                                                 20


<210> SEQ ID NO 4
<211> LENGTH: 20
<212> TYPE: DNA
<213> ORGANISM: Artificial Sequence
<220> FEATURE:
<223> OTHER INFORMATION: Primer VR

<400> SEQUENCE: 4

attaccgcct ttgagtgagc                                                 20
```